United States Patent
Helmer et al.

(10) Patent No.: US 9,707,352 B2
(45) Date of Patent: Jul. 18, 2017

(54) DRUG DELIVERY DEVICE AND METHOD FOR A DRUG DELIVERY DEVICE

(71) Applicant: SANOFI-AVENTIS DEUTSCHLAND GMBH, Frankfurt am Main (DE)

(72) Inventors: Michael Helmer, Frankfurt am Main (DE); Christoph Eisengarthen, Ginsheim (DE); Winfried Huthmacher, Frankfurt (DE); Carsten Mosebach, Mainz (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 419 days.

(21) Appl. No.: 14/346,507

(22) PCT Filed: Sep. 27, 2012

(86) PCT No.: PCT/EP2012/069032
§ 371 (c)(1),
(2) Date: Mar. 21, 2014

(87) PCT Pub. No.: WO2013/045527
PCT Pub. Date: Apr. 4, 2013

(65) Prior Publication Data
US 2014/0236096 A1    Aug. 21, 2014

(30) Foreign Application Priority Data

Sep. 29, 2011    (EP) ..................... 11183300

(51) Int. Cl.
*A61M 5/24*    (2006.01)
*A61M 5/315*    (2006.01)
*A61M 5/31*    (2006.01)

(52) U.S. Cl.
CPC .......... *A61M 5/31536* (2013.01); *A61M 5/24* (2013.01); *A61M 5/31511* (2013.01);
(Continued)

(58) Field of Classification Search
CPC ............ A61M 5/24; A61M 2005/2407; A61M 5/31541; A61M 5/31551; A61M 5/31585;
(Continued)

(56) References Cited

U.S. PATENT DOCUMENTS

| | | | |
|---|---|---|---|
| 4,492,576 A | * | 1/1985 | Dragan ................ A61C 9/0026 433/90 |
| 5,514,097 A | * | 5/1996 | Knauer ................... A61M 5/20 604/136 |

(Continued)

FOREIGN PATENT DOCUMENTS

| | | |
|---|---|---|
| WO | 2008058666 A1 | 5/2008 |
| WO | 2010063707 A1 | 6/2010 |

(Continued)

OTHER PUBLICATIONS

Form PCT/IPEA/416, Notification of Transmittal of the International Preliminary Report on Patentability.

*Primary Examiner* — Nathan R Price
*Assistant Examiner* — Gerald Landry, II
(74) *Attorney, Agent, or Firm* — McDonnell Boehnen Hulbert & Berghoff LLP

(57) ABSTRACT

A drug delivery device is provided comprising a housing comprising a distal end and a proximal end and a cartridge adapted and arranged to contain at least one dose of a drug, a bung being movably arranged within the cartridge. In an initial state of the device, the bung is arranged in a proximal end position with respect to the cartridge. The device further comprises a piston rod adapted and arranged to move the bung in the distal direction with respect to the cartridge for delivering a dose of the drug. The device further comprises a mechanism operable such that, after a dose delivery operation was completed, the piston rod is moved into the proximal direction with respect to the bung by a back off distance (D), wherein in the initial state, a distance between (Continued)

a distal end of the piston rod and a proximal end of the bung is greater than zero, with the distance between the piston rod and the bung in the initial state being defined by the back off distance (D). Furthermore, a method for assembling a drug delivery device is provided.

8 Claims, 8 Drawing Sheets

(52) U.S. Cl.
CPC . *A61M 2005/3103* (2013.01); *A61M 2207/00* (2013.01); *Y10T 29/4978* (2015.01)

(58) Field of Classification Search
CPC .............. A61M 5/3156; A61M 5/3158; A61M 2005/3152; A61M 5/31511; A61M 5/31575
USPC .................. 604/68, 207–211, 218, 224, 311
See application file for complete search history.

(56) References Cited

U.S. PATENT DOCUMENTS

| | | | | |
|---|---|---|---|---|
| 5,584,815 | A * | 12/1996 | Pawelka | A61M 5/19 604/135 |
| 5,688,251 | A * | 11/1997 | Chanoch | A61M 5/3146 222/309 |
| 7,517,334 | B2 * | 4/2009 | Jacobs | A61M 5/31555 604/110 |
| 7,850,662 | B2 * | 12/2010 | Veasey | A61M 5/31546 604/207 |
| 2004/0267207 | A1 * | 12/2004 | Veasey | A61M 5/24 604/208 |
| 2006/0206057 | A1 * | 9/2006 | DeRuntz | A61M 5/31551 604/224 |
| 2007/0185458 | A1 * | 8/2007 | Lin Lee | A61M 5/5066 604/197 |
| 2008/0275916 | A1 * | 11/2008 | Bohannon | G06F 17/30563 |
| 2008/0287883 | A1 * | 11/2008 | Radmer | A61M 5/31551 604/211 |
| 2010/0094207 | A1 * | 4/2010 | Boyd | A61M 5/31555 604/68 |
| 2010/0137791 | A1 * | 6/2010 | Plumptre | A61M 5/3146 604/68 |
| 2011/0245780 | A1 * | 10/2011 | Helmer | A61M 5/31515 604/211 |
| 2012/0071836 | A1 * | 3/2012 | Forstreuter | A61M 5/31515 604/208 |
| 2013/0204203 | A1 * | 8/2013 | Mueller | A61M 5/24 604/208 |

FOREIGN PATENT DOCUMENTS

| | | |
|---|---|---|
| WO | 2011039206 A2 | 4/2011 |
| WO | 2011039236 A1 | 4/2011 |
| WO | 2011051365 A1 | 5/2011 |

* cited by examiner

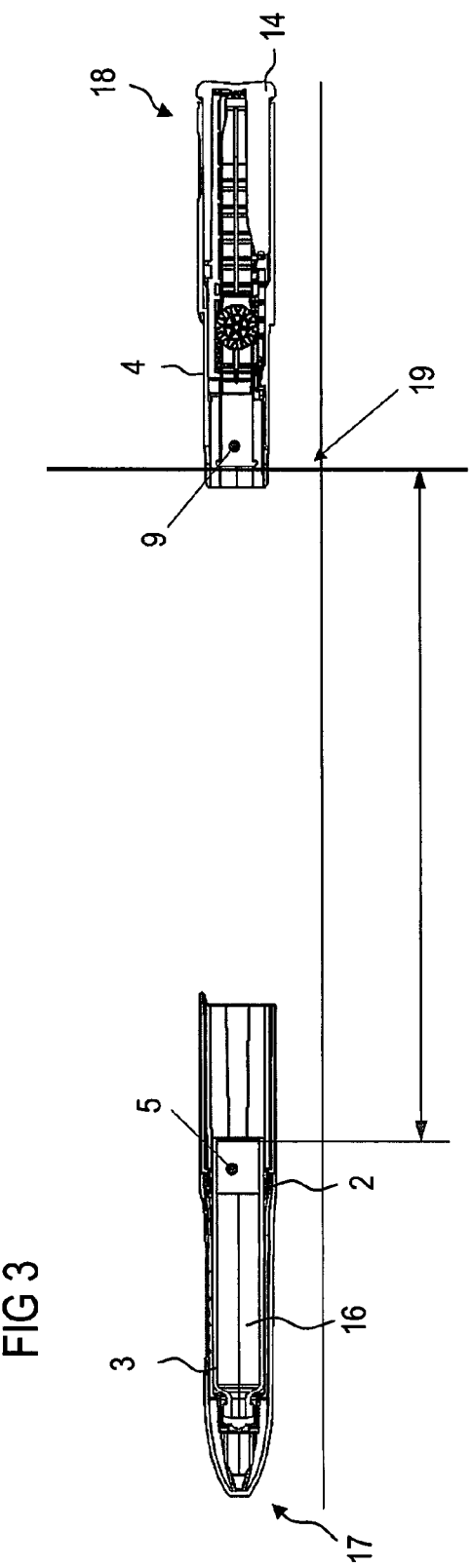

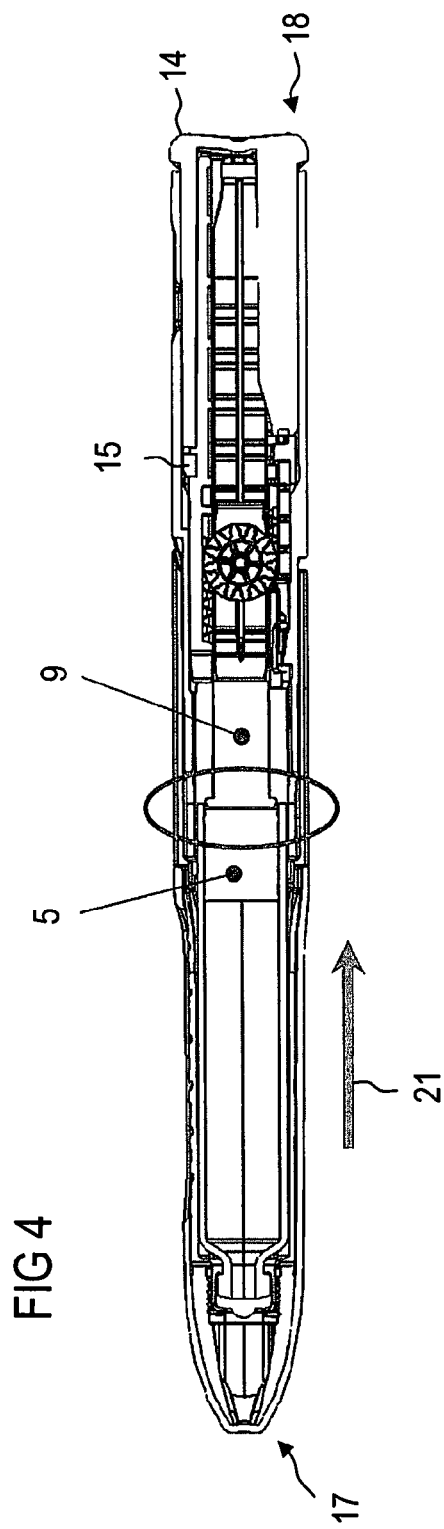

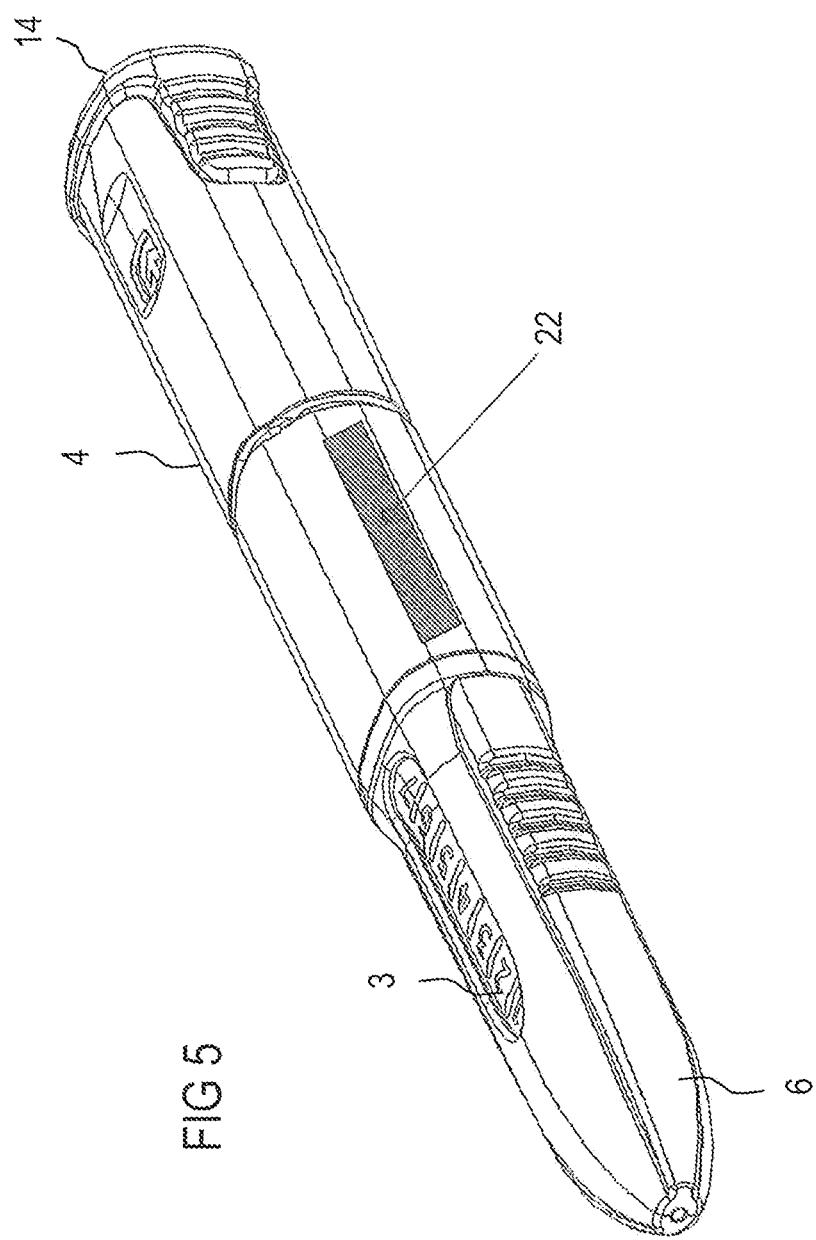

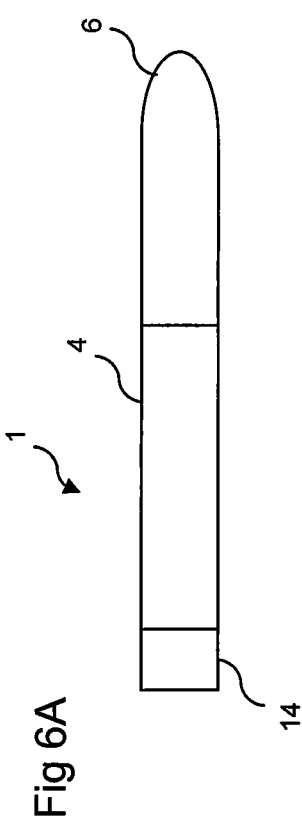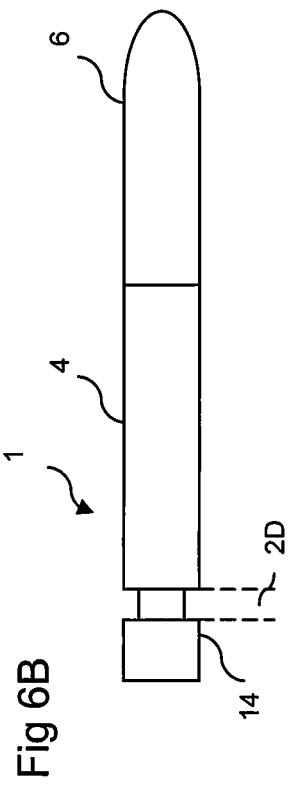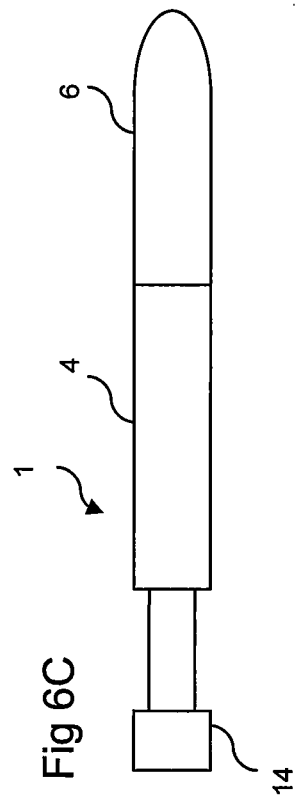

DRUG DELIVERY DEVICE AND METHOD FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2012/069032 filed Sep. 27, 2012, which claims priority to European Patent Application No. 11183300.0 filed Sep. 29, 2011. The entire disclosure contents of these applications are herewith incorporated by reference into the present application.

FIELD OF INVENTION

This disclosure relates to a drug delivery device and a method for assembling a drug delivery device.

BACKGROUND

In a drug delivery device, often, a bung within a cartridge containing a plurality of doses of a drug is displaced by a piston rod. Thereby, a dose of the drug is expelled from the cartridge.

A drug delivery device is described in document WO 2008/058666 A1, for example.

SUMMARY

It is an object of the present disclosure to facilitate provision of an improved drug delivery device. Furthermore, it is an object of the present disclosure to provide a method for assembling an improved drug delivery device.

This object may be achieved by the subject matter of the independent claims. Advantageous embodiments and refinements are subject matter of the dependent claims.

One aspect relates to an assembly for a drug delivery device. The assembly may comprise a housing. The housing may comprise a distal end and a proximal end. The assembly may further comprise a cartridge. The cartridge may be adapted and arranged to contain at least one dose of a drug, preferably a plurality of doses of the drug. A bung may be movably arranged within the cartridge. In an initial state of the device, the bung may be arranged in a proximal end position with respect to the cartridge. The cartridge may be fully filled in the initial state, e.g. no drug has been dispensed yet from the cartridge. The initial state of the device may be state before setting and dispensing a first dose of drug from the cartridge. The initial state may be the state of the device as supplied from the manufacturer. The assembly further comprises a piston rod. The piston rod may be adapted and arranged to move the bung in the distal direction with respect to the cartridge for delivering a dose of the drug. The assembly may comprise a mechanism. Said mechanism may be operable such that, in particular, after a dose delivery operation was completed, the piston rod is moved, preferably automatically moved, into the proximal direction with respect to the bung or away from the bung by a back off distance. Thereby, pressure of the piston rod onto the bung may be reduced. In the initial state, a distance between a distal end of the piston rod and a proximal end of the bung may be greater than zero. The distance between the piston rod and the bung in the initial state may be defined by the back off distance.

The mechanism ensures that, after a dose delivery operation was completed, the piston rod is positioned at the back off distance, from the bung. Pressure onto the bung, which may lead to droplets can thus be reduced or even avoided. In particular, the deformed bung may be allowed to relax in the proximal direction after the dose delivery operation was completed. Uncontrolled relaxation of the bung in the distal direction which may result in unintentional waste of the drug from the cartridge can be avoided in this way.

The mechanism may be further configured such that, in the initial state, the piston rod and the bung are separated by a predetermined initial distance. The predetermined initial distance may be equal to the back off distance or may be less than the back off distance. In particular, the mechanism may define the predetermined initial distance between the piston rod and the bung in the initial state to amount to a predefined initial value which depends from the value of the back off distance. The predefined initial value may be in the range of 0.1 mm to 1.0 mm. The predefined initial value may be 0.2 mm, for example. Adjustment or priming steps of the user, for arranging the piston rod at a predetermined distance from the bung before setting and dispensing a first dose from the device may be redundant. Underdosing may be prevented in this way. In particular, if a user skipped a necessary priming step and injected the priming volume instead, this would result in a significant underdose. By making the priming step redundant, this underdosing may be prevented and, thus, dose accuracy may be increased. Furthermore, this may help to reduce the risk of erroneous operation by inexperienced users and, thus, also waste of drug. Also, some over-cautious users tending to carry out a priming step prior to every dose, would not only waste the first dose of drug, but would unnecessarily empty the cartridge, so that that the device cannot deliver the required number of doses. Making the priming step redundant may help avoiding all of these problems.

In the initial state, there is a distance between the piston rod and the bung, the cartridge is not pressurized. Accordingly, if a needle is mounted to the cartridge, there won't be droplets of drug which emerges from the needle due to pressure in the cartridge. Some drugs may be harmful for the user, if they get in contact with the user's skin. The risk of exposing the skin to the drug due to droplets may be reduced or even avoided by the distance between the piston rod and the bung in the initial state.

A further aspect relates to a method for assembling a drug delivery device. The device may be the device as described above. In a first step, a cartridge unit may be provided. The cartridge unit may comprise a cartridge holder. The cartridge unit may comprise a cartridge. The cartridge may be retained in the cartridge holder. The cartridge may hold at least one dose of a drug, preferably a plurality of doses of the drug. A bung may be movably arranged within the cartridge. Preferably, the bung is arranged in a proximal end position with respect to the cartridge. In particular, the cartridge may be in a completely filled state. In a next step, a drive unit may be provided. The drive unit may be releasable or non-releasably connectable to the cartridge unit. The drive unit may comprise a piston rod. The drive unit may further comprise a mechanism. The mechanism may be configured to move the piston rod by a back off distance when the mechanism switches from an activated state into a deactivated state. In a next step, the mechanism may be activated. In a next step, the position of the proximal end of the bung with respect to a predetermined reference point on the cartridge unit, e.g. a mark on the cartridge holder in which the cartridge is retained, may be measured, in particular when the mechanism is activated. In a next step, the position of the distal end of the piston rod with respect to a predetermined reference point on the drive unit, e.g. a mark on a housing, may be measured. In a next step, information indicative for a relative position of the distal end of the piston rod and the proximal end of the bung may be derived from the results of the previous measurements. In a next step, the mechanism may be deactivated such that the piston rod is displaced by the back off distance. In a next step, the cartridge unit and the drive unit may be connected to one another such that the piston rod and the bung are arranged at an initial distance from one another when the mechanism is deactivated.

In one embodiment, deriving the information comprises determining from the results of the measurements a connecting position for a connection of the cartridge unit and the drive unit such that if the units are connected in the connecting position, the piston rod and the bung are arranged at the initial distance from one another when the mechanism is deactivated. In this case, the cartridge unit and the drive unit may be connectable to one another by a weld. Thereby, the cartridge unit and the drive unit can be brought into variable relative positions for connecting the cartridge unit and the drive unit to one another. In particular, neither the cartridge unit nor the drive unit may comprise a connecting means having a fixed position with respect to the respective unit for connecting the cartridge unit and the drive unit to one another.

According to a further embodiment, deriving the information comprises determining from the results of the measurements a relative position of the proximal end of the bung and the distal end of the piston rod if the cartridge unit and the drive unit were connected by connecting means provided on the cartridge unit and the drive unit. In this embodiment, the cartridge unit and the drive unit may be connectable to one another by a snap-fit connection or a thread. In this case, the cartridge unit and the drive unit may each comprise a connecting means having a fixed position with respect to the respective unit for connecting the cartridge unit to the drive unit. The connecting means of the cartridge unit may comprise a pin, for example. The connecting means of the drive unit may comprise an indentation, for example. Alternatively, the cartridge unit may comprise an indentation and the drive unit may comprise a pin for establishing the snap-fit connection between the cartridge unit and the drive unit. Alternatively, the cartridge unit may comprise a thread and the drive unit may comprise a mating thread.

The previously described mechanism may be configured such that, when the mechanism is in the activated state and the device is fully assembled, the distal end of the piston rod abuts the proximal end of the piston or is arranged at a distance with respect to the proximal end. The mechanism may be configured such, when the mechanism is in the activated state, the bung may be not deformed or compressed or it may be only slightly compressed by the piston rod. The mechanism may be configured such that, when the mechanism is in the activated state, mutual abutment of the bung and the piston rod may be such that the piston rod does not yet apply substantial pressure or thrust to the bung in order to prevent generation of droplet. Droplets may occur if the drug in the cartridge is pressurized and a needle unit is connected to the cartridge unit, thereby establishing fluid communication between the cartridge unit and the environment.

When the mechanism is in the activated state, play between elements of the drive unit may be reduced to a minimum, e g because all of the components are pushed distally with respect to the housing. Accordingly, the measurement is very reliable as all components comprise a well defined or biased position during the measurement. Accordingly, the relative positions of the components after the assembly was completed will also be well defined. Additionally, user operated priming steps may be redundant as the initial distance between the piston rod and the bung may be adjusted very precisely during the assembly process.

When the device is fully assembled and in the initial state with the mechanism being deactivated, there may be no abutment between the piston rod and the bung. In particular, the bung and the piston rod may be arranged at a predetermined initial distance from one another. The predetermined initial distance may be smaller than or equal to the back off distance. By arranging the piston rod at the predetermined initial distance, a user-performed priming step in order to ensure, that the bung and the piston rod are located at a predetermined position with respect to each other, thus ensuring, that with a first dose setting and a subsequent dose dispensing step, a predefined amount of the drug is dispensed, may be redundant. Dose accuracy of the device may be increased.

According to a preferred embodiment, a drug delivery device is provided comprising:
 a housing comprising a distal end and a proximal end,
 a cartridge adapted and arranged to contain at least one dose of a drug , a bung being movably arranged within the cartridge, wherein in an initial state of the device, the bung is arranged in a proximal end position with respect to the cartridge,
 a piston rod adapted and arranged to move the bung in the distal direction with respect to the cartridge for delivering a dose of the drug.

The device further comprises a mechanism operable such that, after a dose delivery operation was completed, the piston rod is moved into the proximal direction with respect to the bung by a back off distance, and wherein in the initial state, a distance between a distal end of the piston rod and a proximal end of the bung is greater than zero, with the distance between the piston rod and the bung in the initial state being defined by the back off distance.

According to a preferred embodiment, a method for assembling a drug delivery device is provided, the method comprising the following steps:
 A) providing a cartridge unit comprising a cartridge which holds at least one dose of a drug, a bung being movably arranged within the cartridge,
 B) Providing a drive unit which is connectable to the cartridge unit, the drive unit comprising a piston rod and a mechanism, wherein the mechanism is configured to move the piston rod by a back off distance when the mechanism switches from an activated state into a deactivated state,
 C) activating the mechanism,
 D) measuring the position of the proximal end of the bung with respect to a predetermined reference point on the cartridge unit,
 E) measuring the position of the distal end of the piston rod with respect to a predetermined reference point on the drive unit,
 F) deriving, from the results of the measurements performed in steps D) and E), information indicative for a relative position of the distal end of the piston rod and the proximal end of the bung
 G) deactivating the mechanism such that the piston rod is displaced by the back off distance,
 H) connecting the cartridge unit and the drive unit to one another such that the piston rod and the bung are arranged at an initial distance from one another when the mechanism is deactivated.

By means of the activated mechanism, play between moveable components of the device may be removed. Accordingly, a very reliable measurement is enabled which results in a device of high dose accuracy without a priming step which has to be carried out by the user.

Of course, features described above in connection with different aspects and embodiments may be combined with each other and with features described below.

BRIEF DESCRIPTION OF THE DRAWINGS

Further features and refinements become apparent from the following description of the exemplary embodiments in connection with the accompanying figures.

Like elements, elements of the same kind and identically acting elements may be provided with the same reference numerals in the figures.

DETAILED DESCRIPTION

Figure 1:
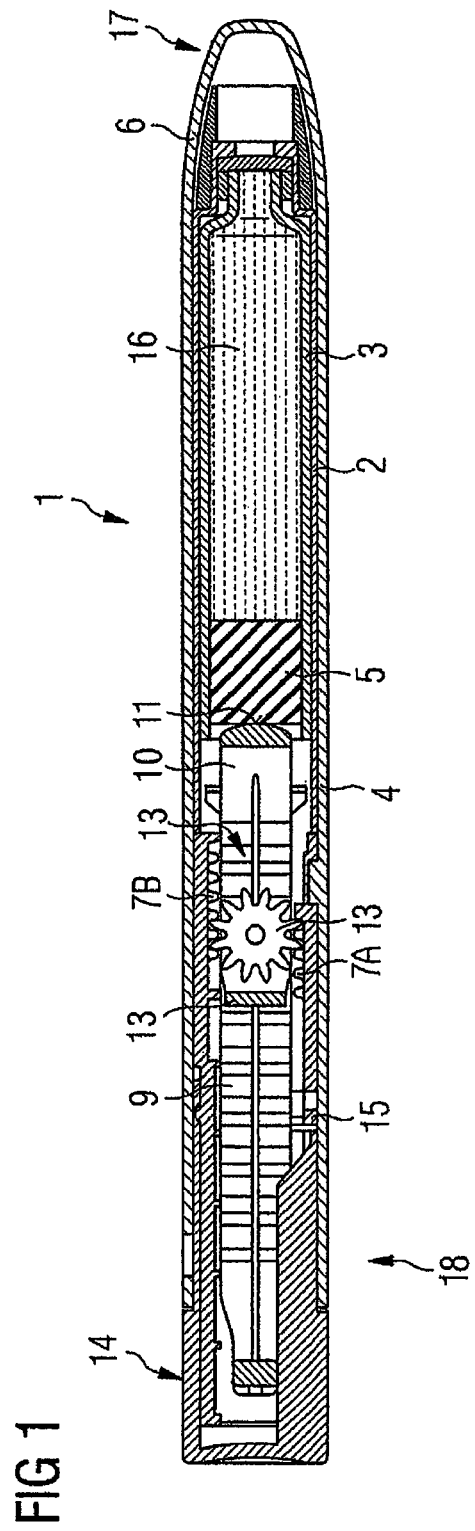
FIG. 1 schematically shows a sectional side view of a drug delivery device.
Figure 2:
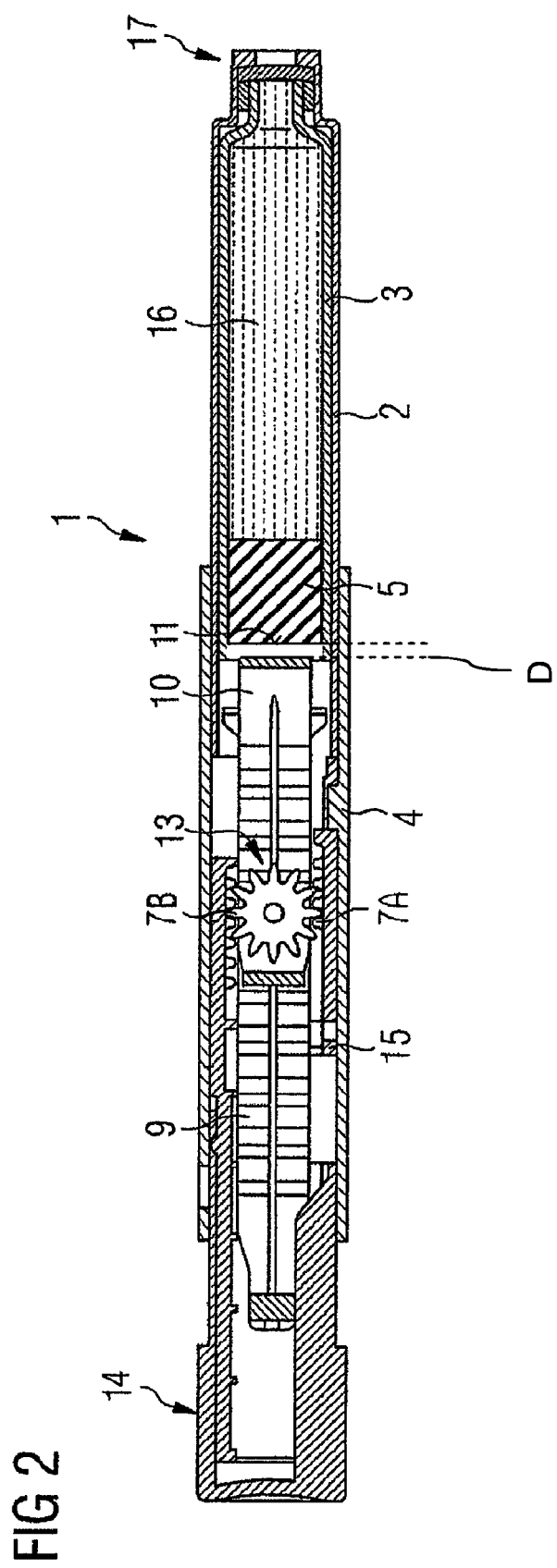
FIG. 2 schematically shows a sectional side view of the drug delivery device of FIG. 1 after a dose setting operation was performed, FIG. 3 schematically shows a sectional side view of the drug delivery device of FIG. 1 during assembly, FIG. 4 schematically shows the drug delivery device of FIG. 3 after assembly was completed, FIG. 5 schematically shows a perspective side view of the assembled drug delivery device of FIG. 5, FIGS. 6A to 6C schematically show a sectional side view of parts of the drug delivery device of FIG. 1 in different states of operation, FIGS. 7A and 7B schematically show a perspective side view of parts of the drug delivery device of FIG. 1, FIG. 7C schematically shows a sectional side view of the parts of the drug delivery device shown in FIGS. 7A and 7B, FIG. 7D schematically shows a bottom view of the parts of the drug delivery device shown in FIGS. 7A to 7C.
Figure 7A:
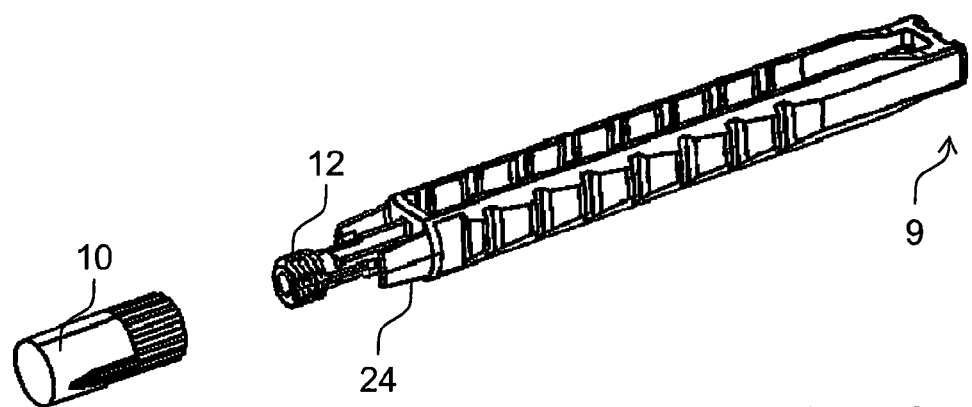
Figure 7B:
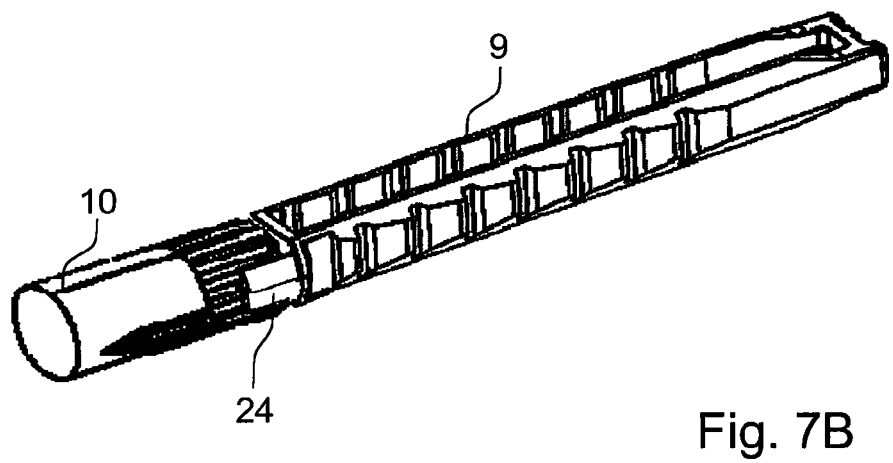
Figure 7C:
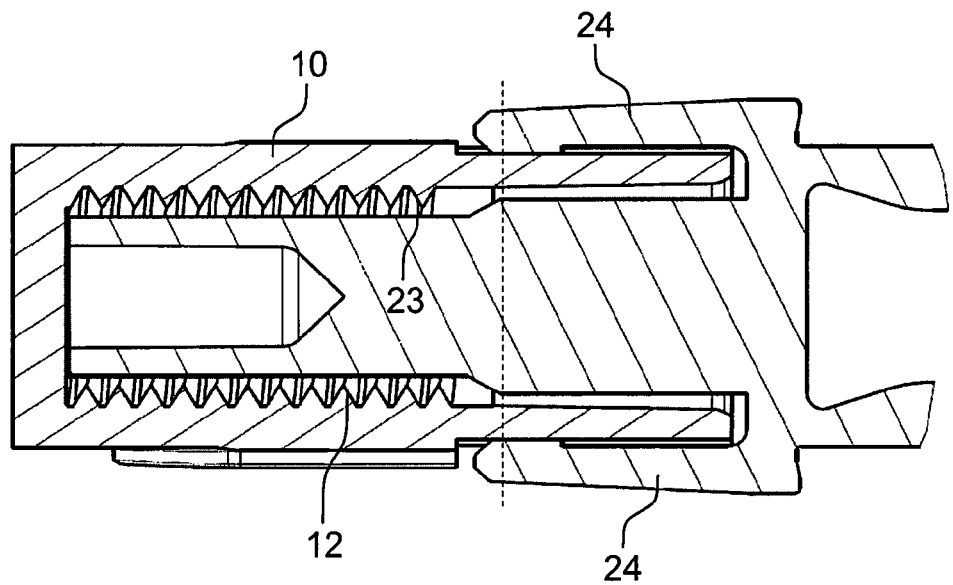
Figure 7D:
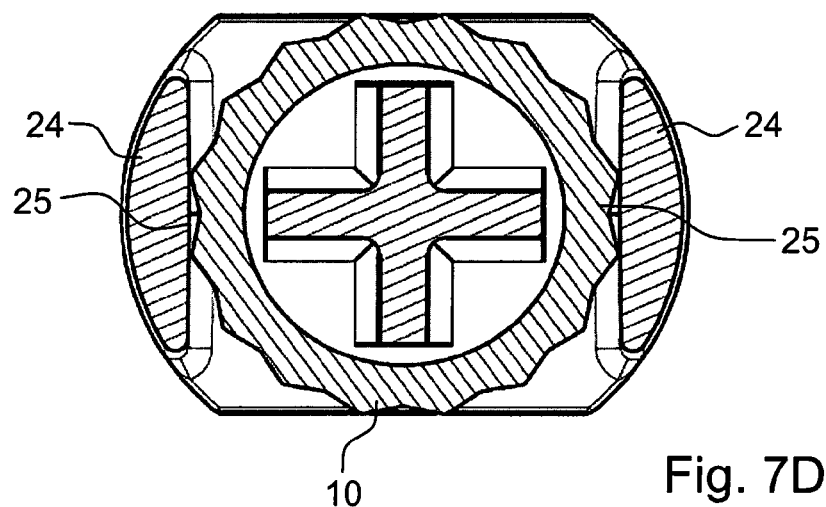

In FIGS. 1 and 2 a drug delivery device 1 is shown. The drug delivery device 1 comprises a housing 4. The drug delivery device 1 and the housing 4 have a distal end and a proximal end. The distal end is indicated by arrow 17. The proximal end is indicated by arrow 18. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1. The distal end and the proximal end are spaced apart from one another in the direction of an axis. The axis may be the longitudinal axis of the device 1.

The drug delivery device 1 comprises a cartridge holder 2. The drug delivery device 1 comprises a cartridge 3. The cartridge 3 is retained within the cartridge holder 2. The cartridge holder 2 stabilizes the position of the cartridge 3 mechanically. The cartridge holder 2 is connectable, e.g. by a threaded engagement, by a weld or by a snap-fit, to the housing 4. The cartridge holder 2 and the housing 4 are irreleasably connected to one another. A cap 6 can be secured to the drug delivery device 1 for protecting the device 1, and, in particular, the cartridge holder 2 or the cartridge 3 from environmental influences, e.g. when the device 1 is not used.

The cartridge 3 contains a drug 16, preferably a plurality of doses of the drug 16. The term "drug", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antihousing or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39), des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antihousing is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antihousing; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antihousing contains two light chains that are always identical; only one type of light chain, κ or λ, is present per antihousing in mammals.

Although the general structure of all antibodies is very similar, the unique property of a given antihousing is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antihousing fragment" contains at least one antigen binding fragment as defined above, and exhibits essentially the same function and specificity as the complete antihousing of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

A bung 5 is slideably retained within the cartridge 3. The bung 5 seals the cartridge 3 proximally. Movement of the bung 5 in the distal direction with respect to the cartridge 3 causes the drug 16 to be dispensed from the cartridge 3. In an initial state of the device 1, i.e. the state as supplied from the manufacturer before setting and dispensing a first dose, the bung 5 is arranged in a proximal end position with respect to the cartridge 3. The cartridge 3 may be fully filled in the initial state, e.g. no drug 16 has been dispensed yet from the cartridge 3.

The drug delivery device 1 may be a pen-type device, in particular a pen-type injector. The device 1 is preferably configured for dispensing fixed doses of the drug 16, i.e. doses which may not be varied by a user. The device 1 is a re-usable device, which means that the cartridge 3 can be replaced, in particular during a reset operation, by a replacement cartridge for dispensing a plurality of doses from the replacement cartridge. Alternatively, the device 1 may be a disposable device 1 which means that the cartridge 3 is non-releasable connected to the cartridge holder 2.

The device 1 comprises a drive mechanism 7A, 7B, 13, 14. The drive mechanism is used for setting and dispensing a dose of the drug 16. For details of the drive mechanism, it is referred to the previously mentioned document WO 2008/058666 A1.

The device 1 comprises a piston rod 9. The piston rod 9 is configured to operate through the housing 4 of the device 1.

In one embodiment (see FIGS. 1, 2 and 7A to 7D) of the device 1, the length of the piston rod 9 can be varied. This may be achieved by means of an adjusting member 10. The adjusting member 10 may be part of the piston rod 9. The adjusting member 10 may be displaceable disposed on the piston rod 9. The adjusting member 10 may be arranged at the distal end of the piston rod 9. The adjusting member 10 may be connected to the piston rod 9 and can be displaced with respect to the piston rod 9, preferably along the piston rod's longitudinal axis, e.g. in axial direction for enlarging or reducing the length of the piston rod 9 prior to final assembly of the device 1, which is described later on in more detail. In an alternative embodiment, the length of the piston rod 9 is fixed (see embodiment of FIG. 5).

In the embodiment where the length of the piston rod 9 is variable, the adjusting member 10 is interconnected with a distal end section of the piston rod 9 facing towards the bung 5. Consequently, the at least one adjusting member 10 is to be arranged between the piston rod 9 and the bung 5. The adjusting member 10 therefore serves as a kind of interface member intended to compensate variations of the mutual distance and/or relative position of piston rod 9 and the bung 5 that may occur, for instance, due to manufacturing and/or assembly tolerances. The piston rod 9 may further comprise at least one interlock means. The interlock means is adapted to interact with the adjusting member 10 and/or with the piston rod 9 for mutually locking in position the adjusting member 10 and the piston rod 9 in an arbitrary relative position to each other. In particular, the adjusting member's 10 axial position relative to the piston rod 9 can be continuously modified, preferably for eliminating said manufacturing and assembly tolerances. Once the adjusting member 10 has been positioned in a tolerance-eliminating configuration with the piston rod 9, its relative position to the piston rod 9 can be either permanently or releasably locked by way of the at least one interlock means. During a tolerance eliminating procedure, e.g. during the assembly process as described below, the adjusting member 10 and piston rod 9 are mutually displaceable with respect to each other. In other words, they may be telescopically shiftable in axial direction. Once a tolerance-eliminating configuration has been attained, adjusting member 10 and piston rod 9 can be mutually interlocked in such a way, that the piston rod 9 is enabled to transfer a respective thrust or force to the bung 5 required for displacing the bung 5 in distal direction. By having the piston rod 9 and the adjusting member 10 displaceably attached or connected thereto, the overall axial dimension and extension of the piston rod 9 becomes variable, in particular for the purpose of tolerance elimination.

In another preferred embodiment (see FIGS. 7A to 7C), the adjusting member 10 and the piston rod 9 are threadedly engaged in order to axially displace the piston rod 9 and the adjusting member 10 relative to each other. The adjusting member 10 and the piston rod 9 are threadedly engaged by mechanical cooperation of an inner thread 23 of the adjusting member (see FIG. 7C) and an outer thread 12 of the piston rod (see FIGS. 7A and 7C). The tread is preferably self-locking By way of a threaded engagement of adjusting member 10 and piston rod 9, the overall axial dimensions of the piston rod 9 can be modified in a continuous way. Here, the interlock means is further adapted to inhibit self-acting relative rotation of piston rod 9 and adjusting member 10. Hence, the interlock means prevents, that the adjusting member 10 autonomously rotates with respect to the piston rod 9 and vice versa. By way of the threaded engagement, axially directed forces and thrust can be transferred, e.g. from the drive mechanism via the piston rod 9 to the adjusting member 10 and finally to the bung 5.

Since the interlock means is designed for inhibiting self-acting relative rotation of piston rod 9 and adjusting member 10, the interlock means itself may not have to withstand those comparatively large axial forces or respective thrust, which is required to displace the bung 5 in the distal direction.

In a further preferred aspect (see FIG. 7C), the adjusting member 10 comprises a threaded receptacle, which is adapted to receive a correspondingly threaded distal socket portion of the piston rod 9.

In an alternative embodiment (not explicitly shown), the piston rod 9 comprises a threaded receptacle at its distal end section, which is adapted to receive a correspondingly threaded proximal socket portion of the adjusting member 10. Hence, the threaded engagement of piston rod 9 and adjusting member 10 can be generally implemented either way.

In another preferred aspect (see FIG. 7D), the interlock means comprises at least one resiliently biased tongue member 24 which is adapted to engage with a corrugated surface portion 25 of the adjusting member 10 or of the piston rod 9. Preferably, the interlock means may positively engage with a side wall of the receptacle of either the adjusting member 10 or the piston rod 9. Additionally, the interlock means is preferably arranged on that part or component comprising the socket portion.

In another preferred embodiment, the tongue member 24 is arranged laterally offset with respect to the socket portion. With respect to the transverse plane of the piston rod 9 that extends perpendicular to the piston rod's longitudinal axis, the axially protruding socket portion is typically arranged on the centre of the adjusting member 10. Here, the resiliently biased tongue member 24 is arranged and displaced with a lateral or radial offset with respect to the socket portion. Hence, mutual arrangement of socket portion and tongue member 24 is such that a gap is formed there between adapted to receive a side wall section of the receptacle.

In a further preferred embodiment, the radially inwardly facing side wall section of the receptacle is threaded in order to provide threaded engagement with the correspondingly threaded socket portion. The side wall section of the receptacle at its outwardly facing side is preferably corrugated or comprises a ribbed structure, by way of which a kind of positive or frictional engagement of the receptacle and the tongue member can be established in order to inhibit self-acting relative rotation of the receptacle relative to the socket portion.

In alternative embodiments it is also conceivable, that an outwardly facing side wall section of the receptacle is threaded and wherein an inwardly facing side wall section of said receptacle is corrugated or comprises a ribbed surface structure. In such embodiments, the resiliently biased tongue members are preferably arranged radially inward with respect to the threaded engagement of adjusting member 10 and piston rod 9.

Mutual engagement and interaction of resiliently biased tongue members and the corrugated surface provides a kind of snap-in feature. Depending on the overall number of longitudinally extending ribs or corrugations and the pitch of the thread a fine adjustment of piston rod and adjusting member 10 in a sub-millimetres range, preferably in a range of 1/10 mm or even 1/100-mm can be attained.

In a further preferred embodiment (not explicitly shown), threaded and corrugated side wall sections of the receptacle are arranged at least partially offset with respect to each other in axial direction. Moreover, the corrugations or the ribs of said wall section comprise an axial extension substantially corresponding with an overall axial extension of the mutually corresponding threads of receptacle and socket portion.

According to a further embodiment (not explicitly shown), the piston rod 9 comprises at least two tongue members arranged at the piston rod 9 and being axially displaced in proximal direction with respect to the piston rod's distal end section. Here, the tongue members, that are preferably arranged opposite to each other in the transverse plane comprise radially inwardly pointing lug portions that are adapted to engage with the corrugated or ribbed outer side wall section of a proximal end of the adjusting member 10 comprising a cupped receptacle.

In a further aspect (see FIGS. 1 and 2), it is intended, that the adjusting member 10 comprises a contact surface at its distal end section that faces towards a proximal end section 11 of the bung 5 if the drug delivery device 1 is in the initial state. The contact or abutment surface is of substantially plane shape and preferably extends in the transverse plane, hence perpendicular to the axial or longitudinal extension of the piston rod. Preferably, the distally facing outer surface of the cupped receptacle of the adjusting member 10 serves as a contact surface.

In the following, with abutment of the piston rod 9 and the bung 5, it may be meant that the adjusting member 10 abuts the bung 5.

The previously described embodiments of the piston rod 9, the adjusting member 10 and/or the interlock means result in a piston rod with adjustable length, which may be used to compensate manufacturing tolerances as described below. As already described further above, in an alternative embodiment of the device 1, the length of the piston rod 9 may be fixed. In this case, the previously described embodiments may be redundant and tolerances may be compensated by adjusting the position of a connection between the cartridge holder 2 and the housing 4. The elimination of tolerances results in a defined initial position of the piston rod 9 relative to the bung 5 after connection of the cartridge holder 2 and the housing 4 was completed and before the first dose of drug is dispensed from the cartridge 3.

The device 1 comprises a mechanism, in particular a back off mechanism. The mechanism comprises a spring member 15, e.g. a helical coil spring. The spring member 15 is axially secured within the housing 4. The spring member 15 is flexibly mounted within the housing. The spring member 15 is flexible in the axial direction. The spring member 15 is unitarily formed with the housing 4 or with a part 7A of the drive mechanism or with an insert of the housing. By means of the back-off mechanism, the piston rod 9 is moved proximally by a back off distance D after a dose delivery operation was performed, which is described later on in more detail. The back off distance D may be less than 1.0 mm. Preferably, the back off distance D is less than 0.5 mm. The back off distance D may be greater than 0.1 mm. The back off distance D preferably amounts to 0.3 mm, for example.

In the initial state of the device, the proximal end of the piston rod 9 is arranged at a predetermined initial distance from the proximal end of the bung 5. The predetermined initial distance is equal to or smaller than the back off distance D. In particular, the predetermined initial distance may be defined by the back off distance D, which is described in connection with the assembly process of the device 1. The predetermined initial distance amounts to 0.2 mm, for example. Accordingly, in the initial state of the device 1, the piston rod 9 and the bung 5 are arranged at a predetermined initial position with respect to one another. User operated steps, e.g. priming steps, for arranging the piston rod 9 and the bung 5 at a predetermined relative position are redundant.

The device 1 comprises an actuation member 14. The actuation member 14 is arranged at least partly within the housing 4 of the device 1. The actuation member 14 may comprise a dose button. The actuation member 14 may comprise a drive member. The actuation member 14 is displaceable with respect to the housing 4. The actuation member 14 can be positioned in a first position (see FIG. 6A) with respect to the housing 4. The first position may be the most distal position of the actuation member 14 with respect to the housing 4. Alternatively, the actuation member 14 can be positioned in a second position with respect to the housing 4 (see FIG. 6B). The second position of the actuation member 14 may be a back-off or initial position. Alternatively, the actuation member 14 can be positioned in a third position (see FIG. 6C) with respect to the housing 4. The third position may be the most proximal position of the actuation member 14 with respect to the housing 4. The second position is arranged more proximal with respect to the housing 4 than the first position. The third position is arranged more proximally with respect to the housing 4 than the second position.

The actuation member 14 is positioned in the first position after a dose delivery operation was fully completed (see FIG. 1). When the actuation member 14 is in the first position, the mechanism is activated. The actuation member 14 is positioned in the second position before a dose setting operation is initiated, e.g. in the initial state (see FIG. 2). When the actuation member 14 is in the second position, the mechanism is deactivated. The actuation member 14 is positioned in the third position after a dose setting operation was completed. When the actuation member 14 is in the third position, the mechanism is deactivated.

The actuation member 14 is moveable from the second or the third position into the first position for activating the mechanism of the device 1. The actuation member 14 is moveable from the third position into the first position for delivering a set dose of the drug 16. Movement of the actuation member 14 from the third position into the first position is transferred to the piston rod 9 by mechanical cooperation of the actuation member 14 and the piston rod 9.

The actuation member 14 is moveable from the first position, i.e. the most distal position, into the second position, i.e. the back-off or initial position, for deactivating the mechanism of the device 1. Movement of the actuation member 14 for being displaced from the first position into the second position is transferred to the piston rod 9 for displacing the piston rod 9 by the back off distance D, which is described later on in more detail.

The actuation member 14 is further moveable from the second position into the third position for setting a dose of the drug 16. Movement of the actuation member 14 for being displaced from the second position into the third position is prevented from being transferred to the piston rod 9 by mechanical cooperation of the housing 4 and the piston rod 9.

Operation of the back off mechanism is described in the following in connection with the assembly and the operation of the device 1.

For assembling the device 1, the following steps are performed. The steps may be, but need not necessarily be performed in the order given below. Note that the subsequently described steps apply for the case that the length of the piston rod is adjustable. This is in the following referred to as embodiment "A". The case in which the position of a connection between the housing 4 and the cartridge holder 2 may be varied to compensate tolerances which does not require a piston rod 9 with adjustable length is in the following referred to as embodiment "B" and is described later on.

A.1) In a first step, the cartridge holder 2 containing the cartridge 3 is provided. The cartridge 3 is in a completely filled state. In particular, the bung 5 is arranged in the proximal end position with respect to the cartridge 3.

A.2) In a second step, the housing 4 with the actuation member 14, the spring member 15 and the piston rod 9 being retained therein is provided. The actuation member 14 is in the second position, the mechanism thus being deactivated. In particular, the spring 15 is in a relaxed state. The housing 4 is not yet connected to the cartridge holder 2.

A.3) In a next step, the previously mentioned back off mechanism is activated. This is achieved by moving the actuation member 14 distally from the second position into the first position. The distance by which the actuation member 14 is moved distally amounts to 0.6 mm, for example. The distance may be greater than 0.1 mm. The distance may be smaller than 2.0 mm. The actuation member 14 is moved against a proximally directed force provided by the spring member 15. Accordingly, the spring member 15 is biased when the actuation member 14 is moved distally. When the actuation member 14 is moved into the first position, the piston rod 9 is moved distally, as well. The piston rod 9 is moved distally by half of the distance by which the actuation member 14 is moved distally, for example. The piston rod 9 is moved distally by 0.3 mm, for example. Accordingly, the mechanical advantage of the device 1 amounts to 2:1 (see embodiments of "rack and pinion" in document WO 2008/058666 A1). When the actuation member 14 is positioned in the first position, the back off mechanism is fully activated.

A.4) In a next step, the position of the proximal end of the bung 5 with respect to a predetermined reference point on the cartridge unit is measured. The reference point can be located on the cartridge 3 or on the cartridge holder 2, for example (see FIG. 3).

A.5) In a next step, the position of the distal end of the piston rod 9 with respect to a predetermined reference point 19 on the housing 4 is measured (see FIG. 3).

A.6) In a next step, the relative position which the proximal end of the bung 5 and the distal end of the piston rod 9 would have when the cartridge holder 2 and the housing 4 were connected, with the mechanism being activated is calculated from the results of the measurements performed in the two previous steps (steps A.4) and A.5)), e.g. based on the known and reliable dimensions of the cartridge holder 2 and the housing 4, the measured values and the position of the marks on the cartridge holder 2 and the housing 4. This relative position is preferably such that, when the mechanism is activated and the device 1 is fully assembled, the bung 5 is not compressed or only minimally compressed by the piston rod 9. The relative position is preferable such that, when the mechanism is activated and the device 1 is fully assembled, the bung 5 and the piston rod 9 just abut one another, or there is a small distance between them.

A.7) In a next step, the mechanism is deactivated. This is achieved by releasing the actuation member 14. Once released, the actuation member 14 is automatically moved from the first position into the second position due to the proximally directed force exerted onto the actuation member 14 by the spring member 15. Movement of the actuation member 14 from the first position into the second position is transferred to the piston rod 9 such that piston rod 9 is displaced by the back off distance D. The piston rod 9 is displaced by a back off distance D which amounts to 0.3 mm, for example. When the actuation member 14 is in the second position, the mechanism is fully deactivated.

A.8) In a next step, it is checked whether the relative position calculated in step A.6)

corresponds to a predetermined relative position. The predetermined relative position may be chosen such that, when the mechanism is activated and the device 1 is fully assembled, the bung 5 is not compressed or only slightly compressed by the piston rod 9. Hence, the predetermined relative position should be chosen such that mutual abutment of the bung 5 and the piston rod 9 is such that the piston rod 9 does not yet apply substantial pressure or thrust to the bung 5 in order to prevent generation of droplet.

A.9) If the relative position which was calculated in step A.6) does not correspond to the predetermined relative position (see step 8)), the length of the piston rod 9 may be varied as described above.

If the relative position which was calculated in step A.6) is such that there would be a gap between the distal end of the piston rod 9 and the proximal end of the bung 5 when the mechanism is activated and the device 1 finally assembled, the length of the piston rod 9 is enlarged by screwing the adjusting member 10 in the distal direction with respect to the piston rod 9. Otherwise underdosing could occur, which could have lethal or even fatal consequences for the user.

If, on the other hand, the relative position which was calculated in step A.6) is such that the distance between the proximal end of the bung 5 and the distal end of the piston rod 9 was too small when the device 1 is assembled, the piston rod 9 would strongly compress the bung 5. This could lead to droplets of the drug 16 or even overdosing. Accordingly, in this case the length of the piston rod 9 is reduced by screwing the adjusting member 10 in the proximal direction with respect to the piston rod 9.

After adjusting the length of the piston rod 9, steps A.3) to A.8) are repeated. If then, again, the relative position which was calculated in step A.6) does not correspond to the predetermined relative position, step A.8) is repeated again.

A.10) If, after having performed step A.8) and, optionally, step A.9) the relative position which was calculated in step A.6) corresponds to the predetermined relative position, the cartridge holder 2 and the housing 4 are moved towards each other (arrow 21 in FIG. 4) and connected to one another (see FIG. 4). Thereby, the cartridge holder 2 and the housing 4 are irreleasably connected by threading or snap-fitting to the cartridge holder 2 and the housing 4 to one another. Thereby, the connection means, e.g. two mating threads or two mating snap-fit elements, are arranged at a fixed position with respect to the housing 4 and the cartridge holder 2.

In the following, the steps for assembling the device 1 according to embodiment "B" are described. In embodiment "B", the length of the piston rod 9 may be fixed and the piston rod 9 can not be used to compensate the tolerances.

Concerning the steps B.1) to B.5) it is referred to the steps A.1) to A.5), which also apply for the case that the length of the piston rod 9 is not adjustable.

B.6) In a next step, a connecting position for a connection of the cartridge holder 2 and the housing 4 is determined from the results of the measurements performed in steps B.4) and B.5), e.g. based on the known and reliable dimensions of the cartridge holder 2 and the housing 4, the measured values and the position of the marks on the cartridge holder 2 and the housing 4. Thereby, the connecting position is chosen such that if the housing 4 and the cartridge holder 2 are connected in the connecting position, the piston rod 9 and the bung 5 are arranged at a predetermined initial distance from one another when the mechanism is deactivated. In particular, it is calculated from the measurements performed in steps B.4) and B.5) which connecting position the cartridge holder 2 and the housing 4 should have to achieve the initial distance between the bung 5 and the piston rod 9 when the device 1 is fully assembled. This distance is preferably such that, when the mechanism is activated and the device 1 is fully assembled, the bung 5 is not compressed or only minimally compressed by the piston rod 9. The distance between piston rod 9 and bung 5, when the mechanism is activated, may be zero or greater than zero. The distance is preferably such that, when the mechanism is activated and the device 1 is fully assembled, the bung 5 and the piston rod 9 just abut one another, or there is a small distance between them.

B.7) In a next step, the mechanism is deactivated. Regarding step B.7) it is referred to step A.7) which applies also for the embodiment where the length of the piston rod 9 is not necessarily adjustable.

B.8) In a next step, the cartridge holder 2 and the housing 4 are moved towards each other and connected to one another. Thereby, the cartridge holder 2 and the housing 4 are irreleasably connected by a weld, for example, which is shown in FIG. 5. The cartridge holder 2 and the housing 4 are welded to one another by a laser, for example. The cartridge holder 2 and the housing 4 are welded to one another via a welding surface 22, for example (FIG. 5). This has the advantage that the cartridge holder 2 and the housing 4 can be brought into variable relative positions when connecting the cartridge holder 2 and the housing 4 to one another. Accordingly, the piston rod 9 and the bung 5 can be brought at variable relative initial positions. In particular, by welding the cartridge holder 2 and the housing 4 to one another, variable predetermined initial distances between the piston rod 9 and the bung 4 can be established. This is possible as the welding surface 22 can be applied to various places on the outer surface of the housing 4 and the cartridge holder 2. Accordingly, in this case, adjustment of the length of the piston rod 9 is redundant.

When the cartridge holder 2 and the housing 4 are connected, in particular after having performed step A.10) for embodiment "A", or step B.8) for embodiment "B", the device 1 is fully assembled. Now, the device 1 is in the previously described initial state. The initial distance between the distal end of the piston rod 9 and the proximal end of the bung 5 is greater than zero. The initial distance is defined by the back off distance D the piston rod 9 was moved proximally when the actuation member 14 was moved from the first position into the second position during the assembly process. The distance in the initial state may correspond to the back off distance D.

The device 1 is supplied to the user in the initial state. For operating the device 1, the following steps are performed:

For setting a dose of the drug 16, the user moves the actuation member 14 from the second position into the third position (see FIG. 2). The piston rod 9 is held in its position by mechanical cooperation with the housing 4. The piston rod 9 is arranged at the predetermined initial distance from the bung 5, which, in FIG. 2 corresponds to the back off distance.

For delivering the dose, the user moves the actuation member 14 from the third position into the first position. Movement of the actuation member 14 is thereby transferred to the piston rod 9 for dispensing the dose. When the actuation member 14 is moved distally, the spring member 15 is biased, the mechanism thus being activated. When the actuation member 14 is in the first position, the mechanism is activated. The dose delivery operation is completed when the actuation member 14 is in the first position. This state is depicted in FIG. 1.

The user now releases the actuation member 14. The actuation member 14 is automatically moved from the first into the second position by the spring member 15. Thereby, the mechanism is deactivated. When the actuation member 14 is moved into the second position, the piston rod 9 is moved proximally by the back off distance D. The back off distance D is less than the distance by which the piston rod 9 is moved distally during a dose delivery operation, i.e. when the actuation member 14 is moved from the third position into the first position. The back off distance D amounts preferably to less than 30% of the distance by which the piston rod 9 is moved distally during a dose delivery operation. Now, the device 1 is ready for setting and dispensing a further dose of the drug 16.

The invention claimed is:

1. A drug delivery device comprising:
   a housing comprising a distal end and a proximal end,
   a cartridge adapted and arranged to contain at least one dose of a drug, a bung being movably arranged within the cartridge, wherein in an initial state of the device, the bung is arranged in a proximal end position with respect to the cartridge,
   a piston rod adapted and arranged to move the bung in the distal direction with respect to the cartridge for delivering a dose of the drug,
   wherein the device comprises a mechanism operable such that, after a dose delivery operation is completed, the piston rod is moved into the proximal direction with respect to the bung by a back off distance (D), and wherein in the initial state, a distance between a distal end of the piston rod and a proximal end of the bung is greater than zero, with the distance between the piston rod and the bung in the initial state being defined by the back off distance (D).

2. The device according to claim 1, further comprising an actuation member which is moveable with respect to the housing, wherein, the actuation member is moveable between a first position and a second position, and wherein movement of the actuation member for being displaced from the first position into the second position is transferred to the piston rod for displacing the piston rod by the back off distance.

3. The device according to claim 1, wherein the back off distance (D) is greater than or equal to the distance between the distal end of the piston rod and the proximal end of the bung in the initial state.

4. The device according to claim 2, wherein the actuation member is further moveable between the second position and a third position, in which the actuation member is positioned after a dose setting operation is completed, wherein the third position is arranged more proximally with respect to the housing than the second position.

5. The device according to claim 2, comprising a spring member which is mounted within the housing, wherein the spring member is configured and arranged to exert a force onto the actuation member to move the actuation member from the first position into the second position, thereby moving the piston rod proximally by the back off distance (D).

6. The device according to claim 5, wherein the back off distance (D) is in the range of 0.1 to 1.0 mm.

7. The device according to claim 5, wherein the back off distance (D) is less than the distance by which the piston rod is moved distally during a dose delivery operation.

8. The device according to claim 1, wherein the piston rod is configured such that the axial dimension of the piston rod can be varied.

* * * * *

UNITED STATES PATENT AND TRADEMARK OFFICE
CERTIFICATE OF CORRECTION

PATENT NO. : 9,707,352 B2  
APPLICATION NO. : 14/346507  
DATED : July 18, 2017  
INVENTOR(S) : Michael Helmer et al.

Page 1 of 1

It is certified that error appears in the above-identified patent and that said Letters Patent is hereby corrected as shown below:

On the Title Page

Item (72) Inventors:
Line 2, delete "Eisengarthen" and replace with --Eissengarthen--.

Signed and Sealed this
Twenty-ninth Day of May, 2018

Andrei Iancu
*Director of the United States Patent and Trademark Office*